United States Patent

Peppler

[11] Patent Number: 5,193,534
[45] Date of Patent: Mar. 16, 1993

[54] RESPIRATORY AID GLASSES

[76] Inventor: James H. Peppler, 13653 West Park Dr., Magalia, Calif. 95954

[21] Appl. No.: 684,292

[22] Filed: Apr. 12, 1991

[51] Int. Cl.$^5$ .............. A61M 15/08; A61M 16/00; A62B 7/00
[52] U.S. Cl. .............. 128/207.18; 128/204.18; 128/DIG. 26
[58] Field of Search .............. 128/200.24, 200.26, 128/200.28, 201.12, 202.13, 202.16, 202.27, 203.22, 204.11, 204.18, 205.22, 207.11, 207.13, 207.18, 911, 912, DIG. 26

[56] References Cited

U.S. PATENT DOCUMENTS

| 2,168,705 | 8/1939 | Francisco et al. | 128/207.18 |
| 3,209,755 | 10/1965 | McCarthy et al. | 128/DIG. 26 |
| 4,465,067 | 8/1984 | Koch et al. | 128/DIG. 26 |
| 4,535,767 | 8/1985 | Tiep et al. | 128/207.18 |
| 4,559,941 | 12/1985 | Timmons et al. | 128/207.18 |
| 4,567,888 | 2/1986 | Robert et al. | 128/204.23 |
| 4,708,446 | 11/1987 | Timmons et al. | 128/207.18 |

Primary Examiner—Edgar S. Burr
Assistant Examiner—Kimberly L. Asher

[57] ABSTRACT

Frames for eyeglasses allow passage of oxygen through or along the temples of the eyeglasses to the nose piece of a patient needing glasses and an oxygen supply. A hollow shell frame in one embodiment is sealed and the oxygen passes inside the frame from a double or single attachment of a source tube to the ends of the temple ear pieces. Oxygen is supplied to the patient's nose piece from tubes opening below the frame which extend downward on each side of the nose rest and fasten to a standard insert nose piece or a nose shield through which the patient receives the oxygen. A second embodiment has a tube passed through the temple and inside the frame around the nose piece of the glasses for attachment to the patient's oxygen supply nose piece. A third embodiment has the frame of the glasses structured to support an external oxygen tube.

3 Claims, 4 Drawing Sheets

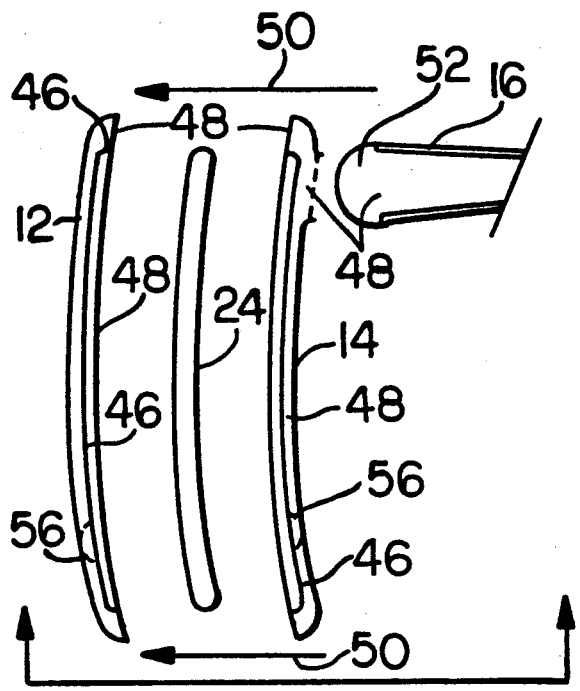
FIG. 2
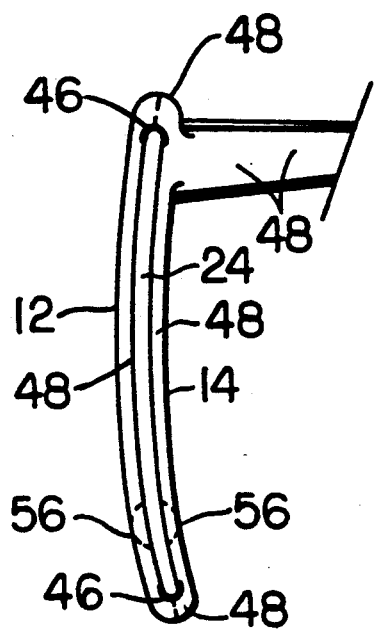
FIG. 3
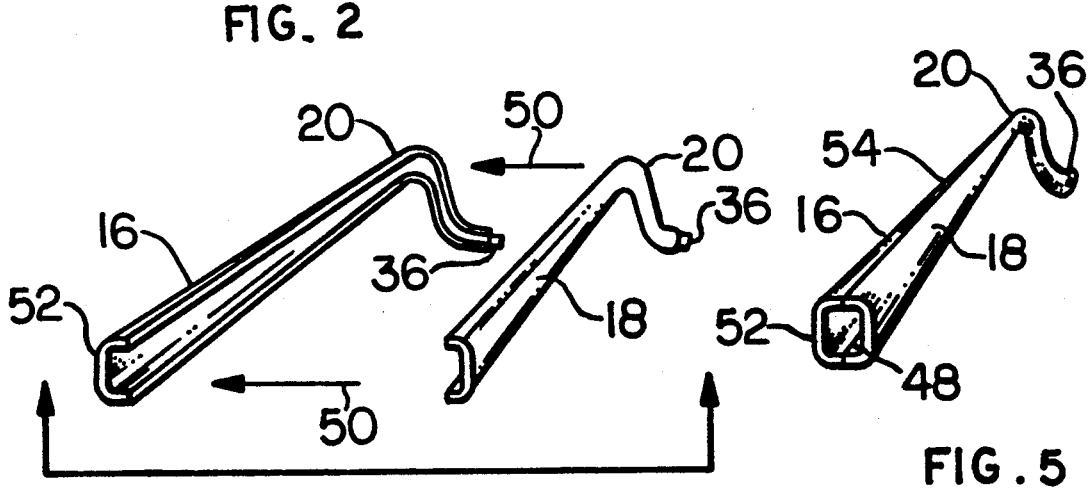
FIG. 4
FIG. 5

RESPIRATORY AID GLASSES

BACKGROUND OF THE INVENTION

1. Field of the Invention

This invention relates generally to respiratory aid appliances. The present invention is particularly directed towards a pair of glasses having the frame adapted to provide support and passageway for oxygen from an oxygen source to a breathing attachment fitted to the nose or covering the nose area of a patient requiring oxygen.

Being deprived of glasses while undergoing oxygen therapy is very uncomfortable for people who wear glasses to read with or even just to see well. The respiratory aid glasses of this invention is designed do overcome this discomfort.

2. Description of the Prior Art

It does not appear that hollow eyeglass frames have been given much consideration in the past art as being useful for directing oxygen from an oxygen source to a patient's oxygen nose piece. Even eyeglasses as a supporting base for the required tubing is not in general use. Some clipping devices, hangers, and other supports are seen which could be used with eyeglasses, but generally, these devices are not used in this manner. In actual practice, the tubing is usually hooked over the patients ears and the source lines dangle across the patient's chest. A patient who needs glasses must cope with this excess of loose tubing in the best way he or she can.

SUMMARY OF THE INVENTION

The present invention is provided to make it easier for patients on oxygen to use glasses. To eliminate loose and floppy tubing wrapped around the patient, I have provided frames for eyeglasses designed for passage of oxygen through or along the temple pieces to the patient's nose piece. In a principal embodiment, the glasses according to the invention have a hollow shell framework through which the oxygen can pass from a double or single attachment of a source tube to the ends of the temple ear pieces. The oxygen supply line can be single or double and attached to the temple pieces in any manner which will charge the hollow frame with oxygen when the source control valve is turned on. The oxygen is supplied to the patient's nose piece from tubes opened into the base of the glasses which extend down below the frame nose piece on each side. These tubes fasten to a standard insert nose piece or a nose shield through which the patient receives the oxygen. For easy manufacturing, in a second embodiment, a tube is inserted through the temple pieces and around the nose piece of the glasses terminating below the lens frame for attachment to the patient's oxygen supply nose piece. A third embodiment has the frame of the glasses structured to support an external tube along the top of one or both temple pieces. The bue then attaches in two places at the top of the eyeglasses lens frame, passes downward inside the lens frame between the nose pads, and exits below the frame as stub ends attachable to the patient's oxygen supply nose piece.

Therefore, a principal object of the invention is to provide a pair of eyeglasses with a frame adapted for passage of oxygen from an oxygen source to a patient's oxygen supply nose piece.

Another object of this invention is to provide eyeglasses for patients who like to read or need eyeglasses to see with but who must have oxygen, the eyeglasses frame being hollow to pass the oxygen through and eliminate the bothersome tubing normally used.

A further object of the invention is to provide eyeglasses as a platform for passage of oxygen from an oxygen source to a patient's oxygen nose piece through tubing inside the framework of the glasses.

A still further object of this invention is to provide eyeglasses with supportive features for passage of oxygen from an oxygen source to a patient's oxygen nose piece through tubing supported principally externally by the frame of the eyeglasses.

Other objects and the many advantages of the present invention will become clear from reading the specification and comparing numerically designated parts described relative to the same numbered parts illustrated in the drawings.

BRIEF DESCRIPTION OF THE DRAWINGS

In the drawings:

FIG. 2 shows the frame of the eyeglasses of FIG. 1 separated from the lens in a sectional side view with the hinge end portion of the hollow temple piece also in a sectional view ready for attachment.

FIG. 3 shows the sections of FIG. 2 attached illustrating the continuous hollow opening formed between the temple piece and the frame of the glasses and around the lens.

FIG. 4 shows two separated temple piece cured sections arranged to be fitted together to form a signal hollow temple piece.

FIG. 5 shows the two sections of FIG. 4 attached.

DESCRIPTION OF THE PREFERRED EMBODIMENTS

Figure 1:
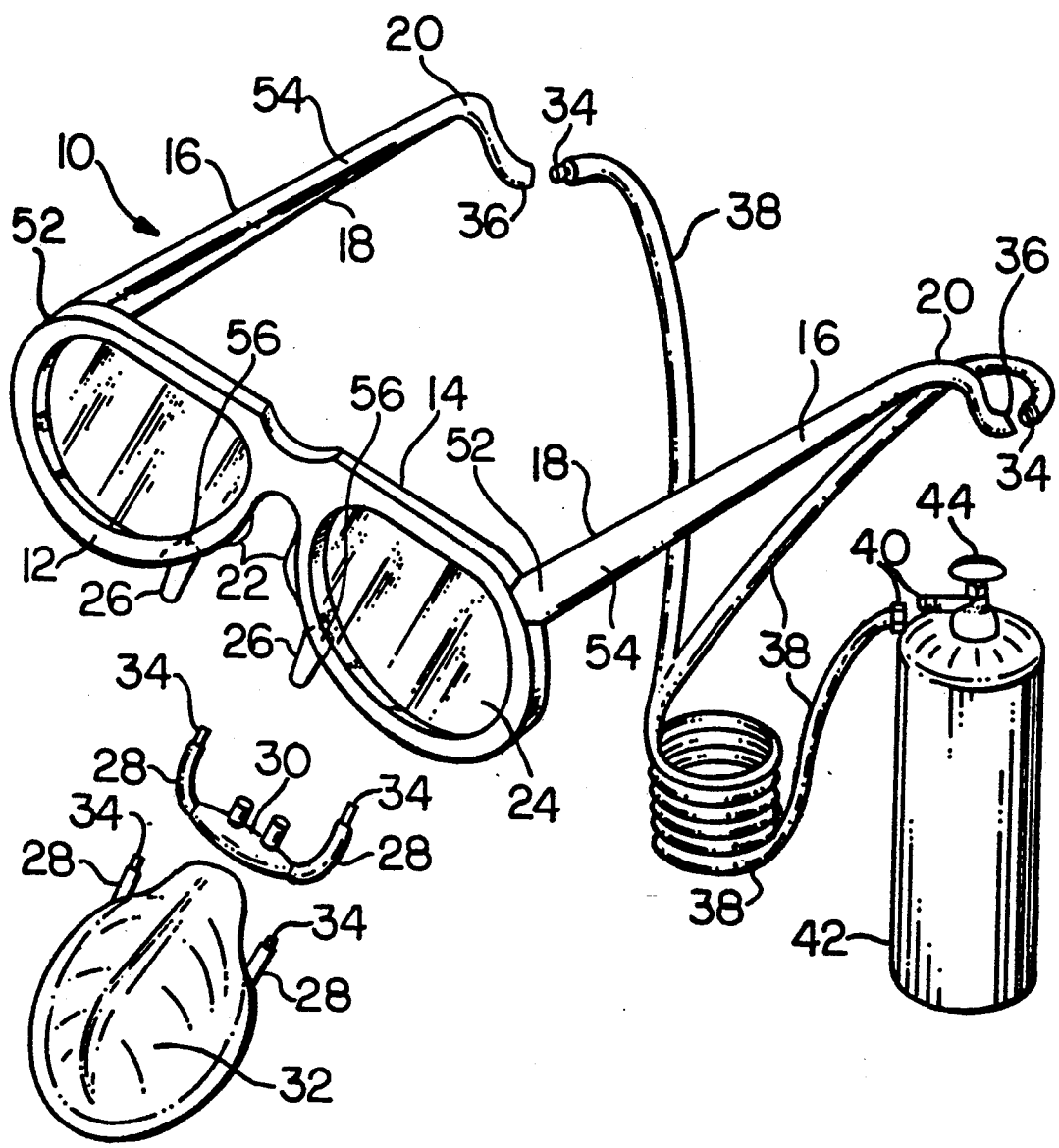
FIG. 1 is a perspective view of eyeglasses having a tubular frame according to the invention in an embodiment that oxygen is passed through the hollow frame to the patient's nose piece.
Figure 6:
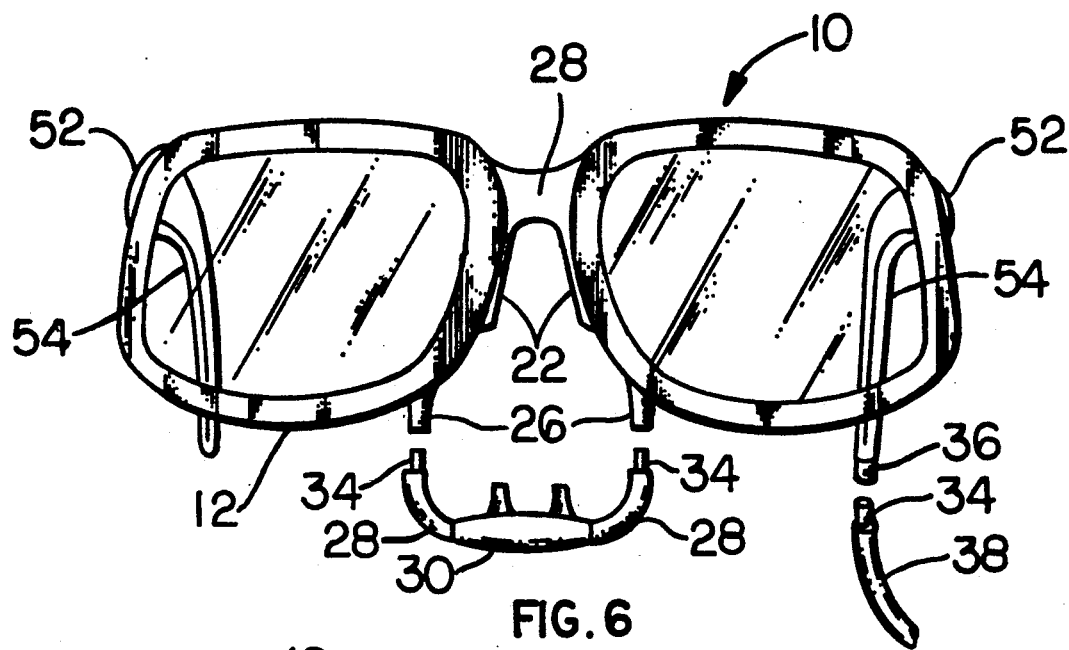
FIG. 6 shows the hollow frame embodiment of the invention in a frontal view illustrating a single oxygen supply line attachment to an ear piece of a single temple piece.
Figure 7:
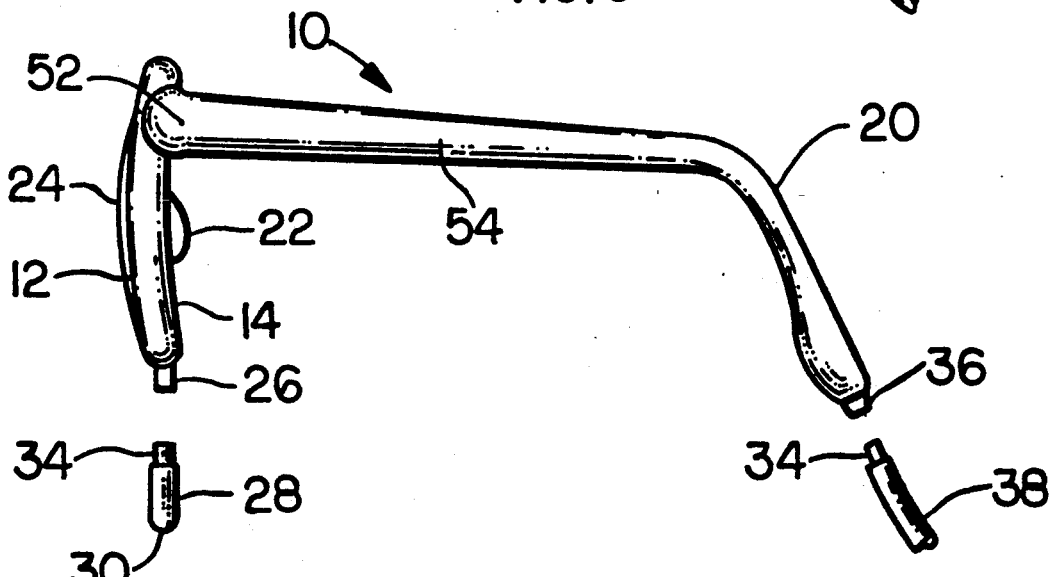
FIG. 7 is a side view of the FIG. 6 embodiment.

Referring now to the drawings at FIG. 1 and FIGS. 2, 3, 4, and 5 where the hollow frame embodiment 10 of the invention is illustrated. Lens 24 is sandwiched between front section lens frame 12 and rear section lens frame 14. Lens 24 is supported by lens rim 46 and the area all around lens rim 46 is a hollow oxygen passageway 48. Hollow oxygen passageway 48 is best seen in FIGS. 2 and 3. Assemblage is illustrated by assemblage directional arrows 50. The assembled invention as shown in FIG. 1 includes two temple pieces 54 which are rigidly attached to frames 12 and 14 at opposite upper outside corners by temple-piece attachment lips 52. Temple piece 54 is structured of two convex section, outer skull temple piece shell 16 and inner skull temple piece shell 18 as shown in FIG. 4. Fitted together, shell 16 and shell 18 provide temple pieces 54 as lead in sections of hollow oxygen passageway 48. See FIG. 5. Oxygen is supplied from oxygen supply line 38 attached to temple pieces 54 at the end of ear rest hooks 20 by tube attachment inserts 34 fitting into temple piece insert receivers 36. For illustrative purposes, FIG. 1, oxygen supply line 38 attaches to oxygen container 42 by oxygen source attachments 40. The required oxygen flow is controlled by oxygen supply control valve 44. In the FIG. 1 illustration, oxygen supply line 38 is branched out from a Y-section and supplies oxygen to both temple pieces 54 at the ends of both ear rest hooks 20. The drawings at FIG. 6 and FIG. 7 illustrate the frame of hollow frame embodiment 10 less lenses 24 in a single line attachment of oxygen supply line 38 to one temple piece 54 only. The Y-connection of FIG. 1 is not used in this application. Eyeglasses hollow nose bridge 58 formed when lens frame sections 12 and 14 are attached allows passage of oxygen along inside the hollow lens frame adjacent both nose pads 22 where the oxygen is released into two frame oxygen supply tubes 26, one adjacent teach side of noose pads 22. The two frame oxygen supply tubes 26 extend a short distance below the two lens frame sections 12 and 14. At the upper ends, frame oxygen supply tubes 26 open into hollow oxygen passageway 48 at oxygen supply frame openings 56, best seen in FIGS. 2 and 3. At the lower ends, frame oxygen supply tubes 26 removably attach to patient nose piece oxygen receiver tubes 28 by tube attachment inserts 34. Patient's insert nose piece 30 can be positioned in the patient's nose area to supply oxygen from oxygen supply line 38 through the hollow sections of temple pieces 54 and between sections 12 and 14 of the frame supporting lens 24. As illustrated in FIG. 1, patient's insert nose piece 30 can be supplemented by patient's full cover nose piece 32. Breathing apparatus like patient's insert nose piece 30 and patient's full cover nose piece 32 are commonly used in systems for supplying oxygen to patients. These devices are shown in the drawings and described in the specification to indicate their use with the present invention which replaces the long lines of oxygen line 38 normally wrapped around the patient.

The FIG. 4 drawing shows the two curved sections, outer skull temple piece section 16 and inner skull temple section 18, positioned to be fitted together to form temple piece 54 and provide hollow oxygen passageway 48 in temple piece 54. The assembled temple piece 54 can be seen in FIG. 5 with temple piece attachment lip 52 positioned where temple piece hinge 70 would normally be. The plastic materials used in hollow frame embodiment 10 according to the invention are sufficiently pliable and resilient to allow temple pieces 54 enough flexibility to fit various patient's head sizes and maintain hollow frame embodiment 10 securely positioned for use on a patient's head. When assembled as shown in FIGS. 1, 6, and 7, hollow frame embodiment 10 has all joints sealed so that oxygen entering through temple insert receivers 36 can only exit through frame oxygen supply tubes 26.

Figure 8:
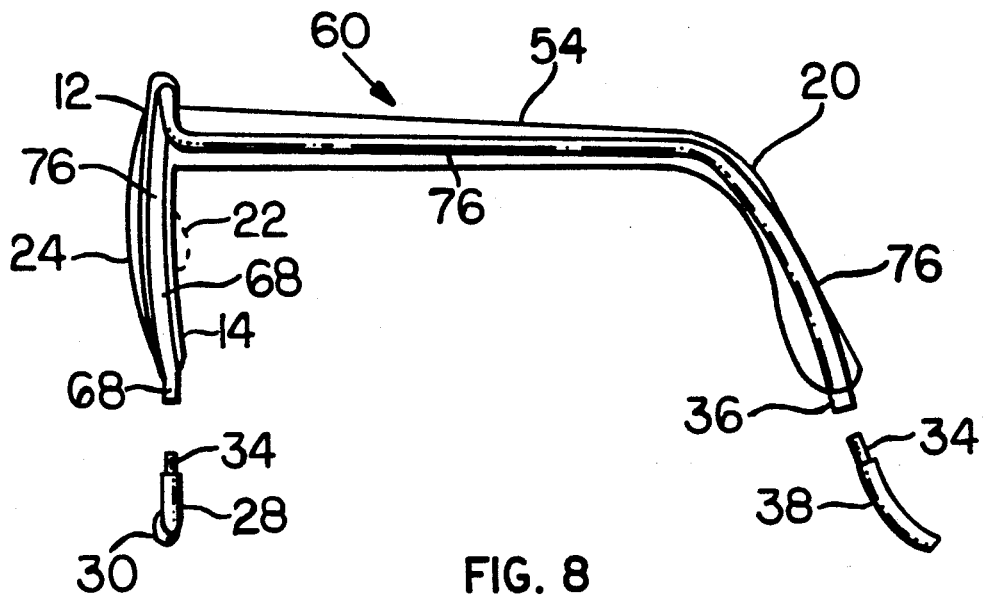
FIG. 8 is a sectional side view of an eyeglasses frame having a tubular insert for the passage of oxygen from the temple-piece ear rest end to the patient's nose clip at the front lower section of the lens frame.

The Fig. 8 drawing shows encased oxygen supply tube embodiment 60. A tubular insert, enclosed oxygen supply line 76, runs inside temple piece 54 from temple piece ear rest hook 20 over lens 24, is divided, and runs down between nose pads 22 to connect with patient insert nose piece 30 at the front lower section of the lens frame formed by front section lens frame 12 and rear section lens frame 14.

Figure 9:
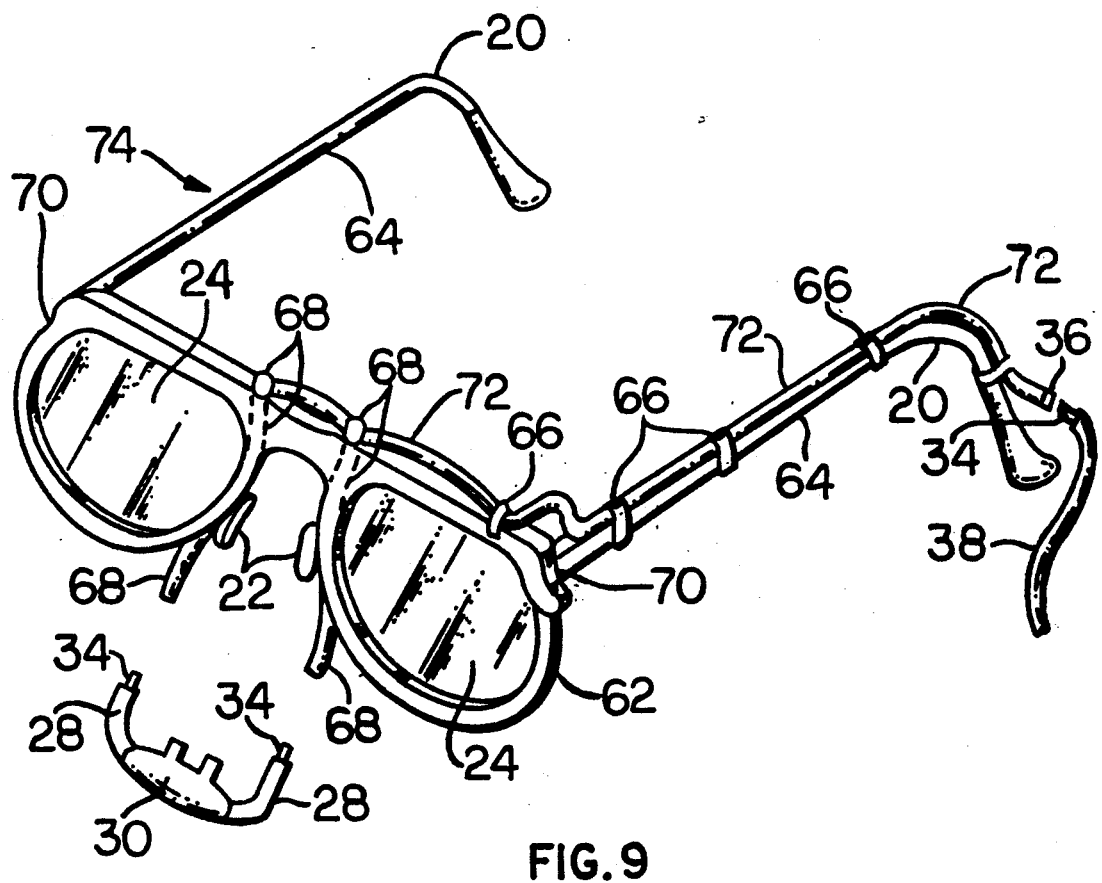
FIG. 9 is a perspective view of an eyeglasses frame designed for external attachment of oxygen passing tubing along the top of the temple piece from an oxygen source fitting to the patient's nose piece immediately below the bridge of the eyeglasses lens frame.

In the FIG. 9 perspective view, solid eyeglasses frame 62 is an embodiment of the invention externally supporting an oxygen passage tube 72 and is designated external tube support frame embodiment 74. Two comfort-cable temple pieces 64 attached by temple piece hinges 70 to the lens frame support oxygen passage tube 72 which is held in position by oxygen tube attachment clips 66. Oxygen passage tube 72 extends along the top of eyeglasses frame 62 where it attaches in two places to two nose piece oxygen passage tubes 68. Nose piece oxygen passage tubes 68 terminates below eyeglasses frame 62 between nose pads 22 fitting to nose piece receiver tubes 28 by tube attachment inserts 34 providing oxygen passageway into patient's insert nose piece 30.

Although I have described embodiments of my invention with considerable detail in the foregoing specification and have illustrated them extensively in the drawings, it is to be understood that I may practice variations in the invention which do not exceed the scope of the appended claims. Also, any variations of my invention practiced by others which fall within the scope of my claims, I shall consider to be my invention.

What is claimed is:

1. An oxygen delivery system comprising a delivery frame, means for delivering oxygen via the delivery frame such that oxygen tubing is not visible within said delivery frame, an oxygen source, oxygen tubing, connection means between said oxygen tubing and said delivery frame, means connecting said delivery frame to the nose of a wearer, wherein said delivery frame comprises two temple pieces each having an end, each temple end having a connector for connection with said means for connecting said oxygen tubing and said delivery frame, each temple piece completely enclosing a respective delivery conduit, said temple pieces each connected to a respective lense frame, each said lense frame enclosing a lense, a hollow passageway extending through each said lense frame completely around each lense, each delivery conduit extending through and completely enclosed by each of said respective lense frames and each said hollow passageway; said delivery frame further comprising a hollow nose bridge, two nose pads, and two oxygen supply members one adjacent each nose pad and in communication with each said lense frame hollow passageway via said hollow nose bridge, wherein said oxygen delivery conduits are completely enclosed within said delivery frame, and said oxygen supply members each being detachably connectable to a respective connection member on a nose piece delivery means.

2. The oxygen delivery system of claim 1, wherein said nose piece delivery means comprises a nasal cannula.

3. The oxygen delivery system of claim 1, wherein said nose piece delivery means comprises a nasal mask.

* * * * *